(12) United States Patent
Haisch

(10) Patent No.: US 7,477,764 B2
(45) Date of Patent: Jan. 13, 2009

(54) EXAMINATION SYSTEM AND EXAMINATION METHOD

(75) Inventor: Michael Haisch, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 1016 days.

(21) Appl. No.: 10/704,647

(22) Filed: Nov. 12, 2003

(65) Prior Publication Data

US 2004/0167742 A1  Aug. 26, 2004

(30) Foreign Application Priority Data

Nov. 13, 2002  (DE) ................ 102 52 837

(51) Int. Cl.
*G06K 9/00* (2006.01)
*G01C 9/00* (2006.01)
(52) U.S. Cl. .................. 382/128; 702/150; 128/922
(58) Field of Classification Search ............... 382/128, 382/129–132; 702/150–153; 128/922
See application file for complete search history.

(56) References Cited

U.S. PATENT DOCUMENTS

| | | | |
|---|---|---|---|
| 4,786,155 A | 11/1988 | Fantone et al. | |
| 5,982,532 A | 11/1999 | Mittelstadt et al. | |
| 6,006,126 A | 12/1999 | Cosman | |
| 6,167,296 A | 12/2000 | Shahidi | |
| 6,191,862 B1 * | 2/2001 | Swanson et al. | ............ 356/479 |
| 6,741,948 B2 * | 5/2004 | Hauger et al. | ............... 702/152 |
| 6,763,259 B1 | 7/2004 | Hauger et al. | |
| 2002/0120424 A1 | 8/2002 | Hauger et al. | |

FOREIGN PATENT DOCUMENTS

| | | |
|---|---|---|
| DE | 36 23 394 C2 | 4/1997 |
| DE | 196 40 907 A1 | 4/1997 |
| DE | 199 30 408 A1 | 1/2001 |
| DE | 100 27 827 A1 | 12/2001 |
| DE | 101 00 335 A1 | 8/2002 |
| WO | WO 99/00052 | 1/1999 |

* cited by examiner

*Primary Examiner*—Aaron W Carter
(74) *Attorney, Agent, or Firm*—Potomac Patent Group PLLC

(57) ABSTRACT

An examination system and a corresponding examination method, comprise: Arranging a tissue region in a vicinity of an object plane of a microscope and generating an optical image of the tissue region, receiving tissue data from a measuring head separate from the microscope, discriminating the tissue data into at least two data categories and displaying markings in the optical image of the tissue region in dependence of the discriminated data category and a relative position between a component of the microscope and the measuring head.

16 Claims, 3 Drawing Sheets

EXAMINATION SYSTEM AND EXAMINATION METHOD

This application claims the benefit of priority application DE102 52 837.3 filed in Germany on Nov. 13, 2002, the subject matter of which is incorporated herein by reference.

BACKGROUND OF THE INVENTION

1. Field of the Invention

The present invention relates to an examination system and an examination method for displaying a tissue region to a user. The tissue region is in particular a portion of a patient to undergo a surgical operation, and the user is in particular a surgeon performing such surgical operation.

2. Brief Description of Related Art

In a conventional surgical system and method, e.g., a near-surface tumor is to be excised from the tissue region, and the surgical operation is performed by a surgeon viewing the tissue region through a surgical microscope. An ultrasound system may be used for localizing the tumor to be excised. The surgeon scans the tissue region in which the tumor is presumed with a measuring head of the ultrasound system, and the surgeon views sampled ultrasonic depth scans on a display device of the ultrasound system. From the depth scans the surgeon can conclude, whether there is any tumor tissue at the location at which the measuring head is presently located. The surgeon then looks through the surgical microscope to perceive such location in the microscope image and memorize the same. By multiply repeating this procedure, the surgeon perceives the extension of the tumor, memorizes the same and can then perform the surgical operation to excise the tumor while looking through the surgical microscope.

This procedure is complicated and requires high concentration on the part of the surgeon, because the success of the operation depends on the extent to which the surgeon can memorize the extension of the tumor.

SUMMARY OF THE INVENTION

It is an object of the present invention to provide a system and a method that may simplify localizing specific tissue types in an image of a microscope.

To solve this object, the invention provides an examination system for displaying a tissue region to a viewer, comprising: an optical system for generating an optical image of the tissue region; a tissue qualifying system having a measuring head for receiving tissue data, and having a computer for analyzing the obtained tissue data and discriminating the obtained tissue data into at least two data categories; a position detecting system configured to determine a position of the measuring head relative to the component of the optical system; and an indicating system for optically marking portions of the optical image of the tissue region based on the detected position of the measuring head and on the discriminated data category.

The data categories may characterize the tissue at those locations at which the measuring head samples tissue data at a particular time. According to an exemplary embodiment, the at least two data categories comprise a "tumor tissue" and a "non-tumor tissue". However, it is also possible that the tissue qualifying system discriminates a higher number or other types of tissue, such as nerves and supporting tissue.

The examination system may enable the user to perceive an extension of a specific type of tissue in the tissue region under examination, without having to avert his view from the image of the tissue region generated by the optical system. This is because the viewer may move the measuring head across the tissue region while observing the optical image thereof, and the examination system may provide the marking or indication of the image at those locations of the image where the tissue qualifying system discriminates a certain data category from the data sampled by the measuring head. Since these markings or indications may be provided directly in the image generated by the optical system, the viewer does not have to avert his view from, e.g., a display for generating the optical image of the tissue region, as this was necessary in the conventional system.

According to a preferred embodiment, it is possible that the marking or indication displayed at a certain location in the image is continued to be displayed at that location even when the measuring head has been further moved and is already sampling data at another location of the tissue region. After systematically scanning the tissue region to be examined, an extended partial region of the image of the tissue region, in which the tissue type of interest is present, is marked by e.g. highlighting, a particular color or other means.

In order to sample the tissue data, various known methods may be employed. According to preferred exemplary embodiments, the measuring head may comprise a fluorescence measuring head, a Raman spectroscopy head, an acousto-optical measuring head, an optical coherence tomography (OCT) measuring head, an ultrasound measuring head, such as an ultrasonic Doppler measuring head, a concentration measuring head, such as a blood glucose concentration measuring head, a sodium concentration measuring head and a potassium concentration measuring head, and a temperature measuring head.

According to a preferred exemplary embodiment, the optical system may comprise a microscope having an objective lens. Herein, the position detection system is preferably configured to determine the position of the measuring head relative to the objective lens.

The microscope preferably comprises a camera to record image data which represent the optical image of the tissue region. A computer can then, by image data processing, recognize the measuring head in the image and calculate its position within the image. At this calculated position, the marking is then displayed, if the tissue data fall into a designated data category.

It is, however, also preferred to additionally provide a position detection system independent of the microscope for evaluating the relative position between the measuring head and the microscope. A conventional triangulation system tracking suitable markings provided at the measuring head is an example for such position detection system. Here it is also possible to evaluate both the position of the microscope relative to the position detection system, and the position of the measuring head relative to the position detection system, and to calculate the relative position between the microscope and the measuring head from the positions of the microscope and the measuring head.

The indication system preferably comprises a display for displaying the marking and a first beam splitter for coupling an image of the displayed marking into a beam path of the microscope, whereby a simultaneous perceptibility of both the optical image generated by the microscope and the marking is made possible.

Where the microscope comprises an ocular lens, the image of the displayed marking is preferably coupled into the beam path between the objective lens and the ocular lens by a first beam splitter.

According to a preferred embodiment the optical system comprises, e.g. for archive purposes, a camera for recording an image coupled out of the beam path between the objective lens and the ocular lens by a second beam splitter. The second beam splitter is preferably provided downstream of the first beam splitter in the beam path, so that in the image recorded by the camera the generated markings are also included.

However, it is also possible that the camera first records an image of the tissue region free of the markings, and that the markings are then electronically introduced into the image recorded by the camera.

In particular, in a case where the position detection system evaluates data of the optical image of the tissue region, in which data markings are provided, it is preferable to provide the markings using color components which are different from those color components which the position detection system evaluates for determining the position of the measuring head.

Besides displaying the optical image of the examined tissue region to the viewer by means of ocular lenses, it is also preferred to display the image to the viewer by a display device which the viewer can wear on his head, such as a head mounted display. Furthermore, the optical image can be displayed on a monitor.

The measuring head can be adapted to sample data at only one location at a time. However, it is also possible that the measuring head samples data at plural locations simultaneously, which are, e.g., arranged on a line or distributed in a two-dimensional array. For the multiple locations, a discrimination according to tissue categories is respectively performed, and a corresponding marking is provided in the optical image of the tissue region.

BRIEF DESCRIPTION OF THE DRAWINGS

The forgoing as well as other advantageous features of the invention will be more apparent from the following detailed description of exemplary embodiments of the invention with reference to the accompanying drawings, wherein.

DETAILED DESCRIPTION OF EXEMPLARY EMBODIMENTS

Figure 1:
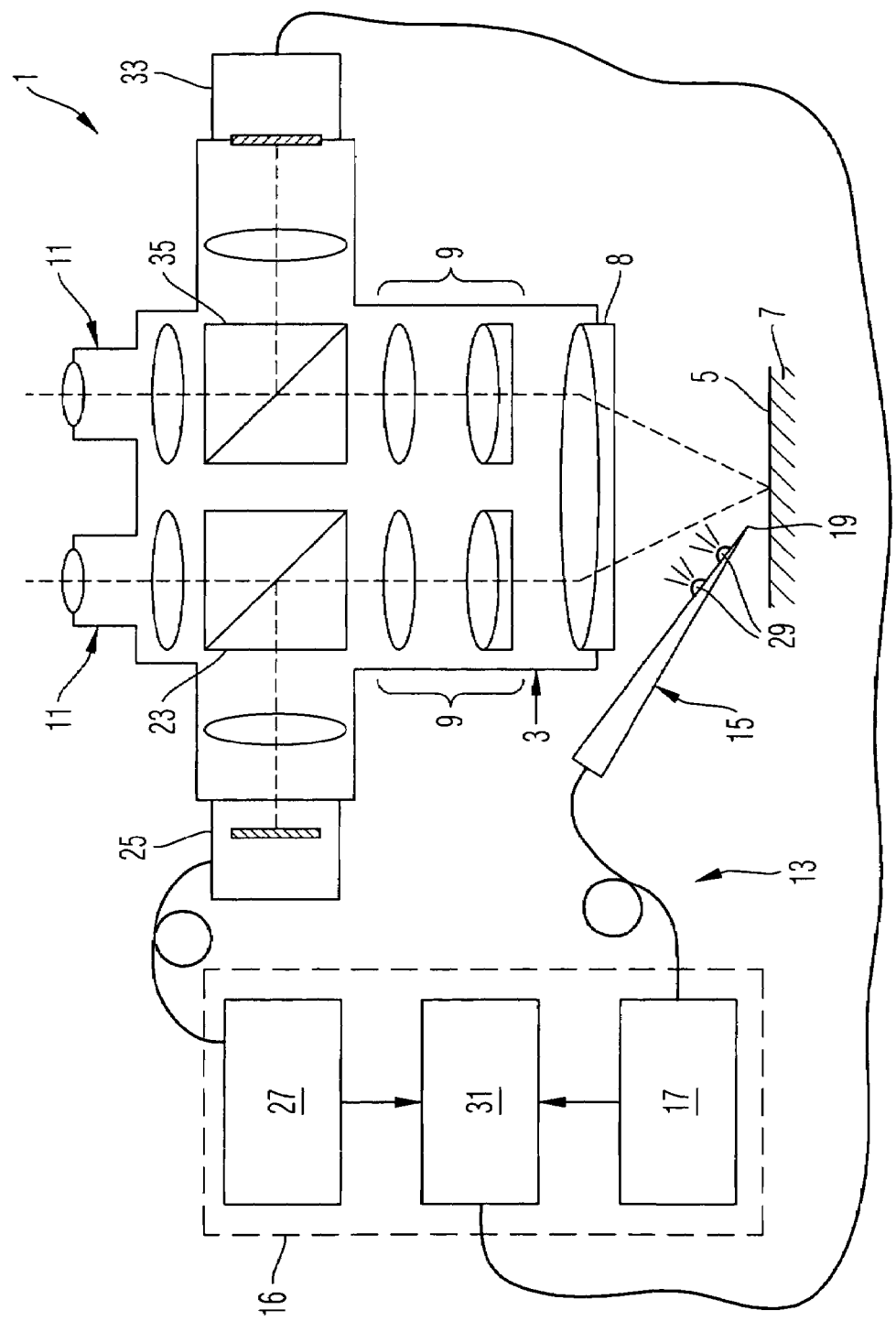
FIG. 1 is a schematic representation of an examination system according to a first embodiment of the present invention.

In the embodiments described below, components which are identical in function and structure are designated as far as possible by the same reference numerals. Therefore, to understand the features of the individual components of a specific embodiment, the descriptions of other embodiments should be referred to.

An exemplary examination system 1 shown in FIG. 1 comprises a surgical microscope 3 for generating a stereo-microscopic image of a tissue area 7 arranged in an object plane 5. To this end, the operation microscope 3 comprises an objective lens 8 and a beam path with two zoom systems 9 for imaging the image of the object plane 5 via two ocular lenses 11 to both the left and right eyes of the viewer.

Figure 3A:
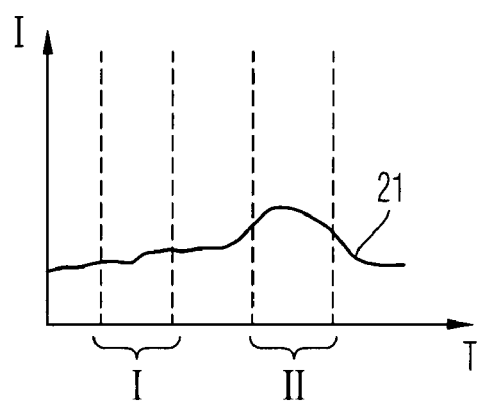
FIG. 3a is a schematic representation of tissue data belonging to two different data categories.

Furthermore, the examination system 1 comprises a tissue qualifying system 13, having an ultrasound measuring head 15 for sampling tissue data and a discriminating device 17 for evaluating the tissue data. The discriminating device 17 may be realized as a software component in a computer 16. The ultrasound measuring head 15 emits ultrasonic waves from a tip 19 of the measuring head and receives ultrasonic waves reflected by the tissue and generates data therefrom, such as depicted by way of example in FIG. 3a for healthy tissue. Therein, a data curve 21 is depicted, which represents the intensity I of ultrasonic waves reflected from the tissue in dependence of the tissue depth T starting from the tissue surface.

Figure 3B:
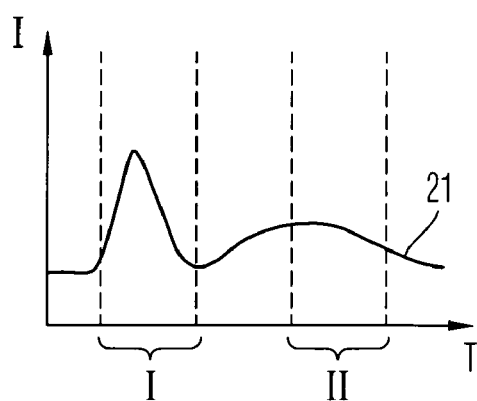
FIG. 3b is a schematic representation of further tissue data belonging to two different data categories.

In FIG. 3b, data are depicted which are sampled by the measuring head when same is located above tumor tissue.

The discriminating device 17 evaluates the data provided by the measuring head and discriminates same into two data categories, namely "tumor tissue" and "non-tumor tissue". The discrimination can be performed, e.g. in such a manner that the computer averages data from regions labeled I and II, respectively, in FIGS. 3a and 3b, and calculates a ratio of the averaged intensity in region I over the averaged intensity in region II. If this ratio is less than one, discrimination as "non-tumor tissue" is made, and if this ratio is equal to or larger than one, discrimination as "tumor tissue" is made.

In the beam path of the stereo-microscope 3 on the left in FIG. 1, a beam splitter 23 is provided between the zoom system 9 and the ocular lens 11. The beam splitter 23 couples a partial beam out of the beam path and supplies it to a camera 25 in such a way that camera 25 detects an image of the object plane 5. The detected image is supplied as image data to an image evaluation device 27, which may be realized as a software component in the computer 16. The measuring head 15 comprises two light emitting diodes 29 at a distance from its tip 19. Light emitted from the diodes 29 is also imaged onto the camera 25 by the left beam path, such that the diodes 29 are also represented in the image data supplied to the image evaluation device 27. The image evaluation device 27 determines the locations of the light emitting diodes 29 relative to the microscope 3 from the image data. Using a predetermined geometrical relation of the two light emitting diodes relative to each other and relative to the tip 19 of the measuring head 15, the position of the measuring head 19 relative to the microscope 3 is determined finally.

The detected position of the measuring head 15 is supplied by the image evaluation device 27 to a marker display device 31, which may also be realized as a software component in the computer 16. The marker display device 31 further receives a signal from the discrimination device 17, whenever same discriminates the data sampled by the measuring head 15 as "tumor tissue". The device 31 then generates image data representing an image which has a marking, such as a green spot, at the position detected by the position detecting device 27. These image data are then submitted to an LCD-display 33 displaying an image representing the image data. The image is coupled into the beam path of the microscope on the right in FIG. 1, by a beam splitter 35 disposed between the zoom system 9 and the ocular lens 11. Thereby, the right eye of the viewer sees a green marking superimposed onto the optical image of the object plane 5 at the position of the tip 19 of the measuring head 15, if the tissue data sampled by same have been discriminated by the discrimination device 17 as "tumor tissue".

Figure 2:
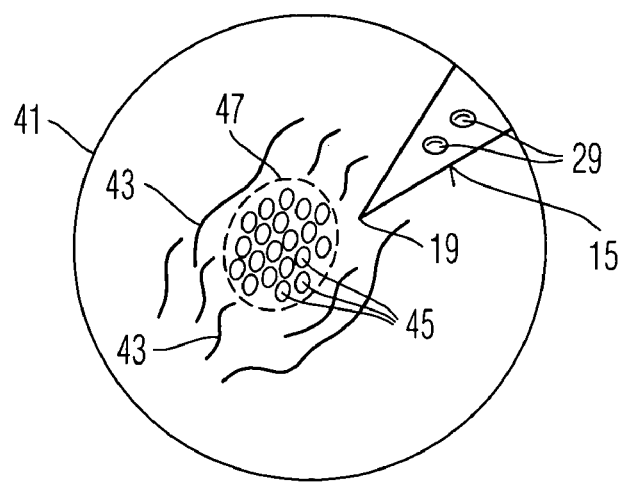
FIG. 2 is a schematic representation of an optical image of an examined tissue region obtained with the examination system of FIG. 1, with markings displayed therein.

In FIG. 2, an image of an object region 41 of the microscope 3 is shown schematically as perceived by a viewer with his right eye when looking through the ocular lens 11. Therein, lines indicate tissue structures as generated by the microscope 3 as an optical image of the examined tissue region. Further, a part of the measuring head 15 with its tip 19 and the two light emitting diodes 29 are visible in the image. In the situation shown in FIG. 2, the tip 19 of the measuring head 15 has already been scanned systematically over the examined tissue region, and markings 45 indicated as small circles are visible and represent tumor tissue. The markings 45 are visible at such locations where the system has detected tissue data of the category "tumor tissue". These markings are stored by the device 31 and thus remain visible in the image even when the tip 19 of the measuring head 15 is no longer in the corresponding place. However, the option is provided to delete the markings previously stored, in order to re-start the examination all over.

Alternatively, or additionally, to the display of the individual markings as circles, it is also possible to display a line, indicated as a dashed line 47 in FIG. 2 as a marking. The line 47 has been calculated by the device 31 so as to represent a periphery of a group of markings 45. This has the advantage that the image of the optically perceivable structures 45 is not excessively overlaid when the markings 45 are not shown in the image.

In the embodiment shown in FIG. 1, the beam splitters 23 and 35 are arranged in the left and right beam path, respectively, of the microscope 3. Alternatively, it is also possible to arrange both beam splitters in one beam path of the microscope in such a way that the beam splitter 35 for coupling in the image generated by the display 33 is arranged between the beam splitter 23 for coupling out the image of the object area 5, and the zoom system 9. In such embodiment, the image recorded by the camera 25 includes the markings generated by the display 33 for e.g. recording purposes or in order to enable further viewers, which have no access to the ocular lenses 11, to view the same image as the viewer looking into the ocular lenses 11.

In order that the markings 45 coupled in may not disturb evaluation of the position of the light emitting diodes 29 by the image evaluation device 27, the markings may be displayed in green, while the evaluation device 27 uses only red image components for evaluation of the position of the measuring head, namely those of the color which the light emitting diodes 29 emit.

Figure 4:
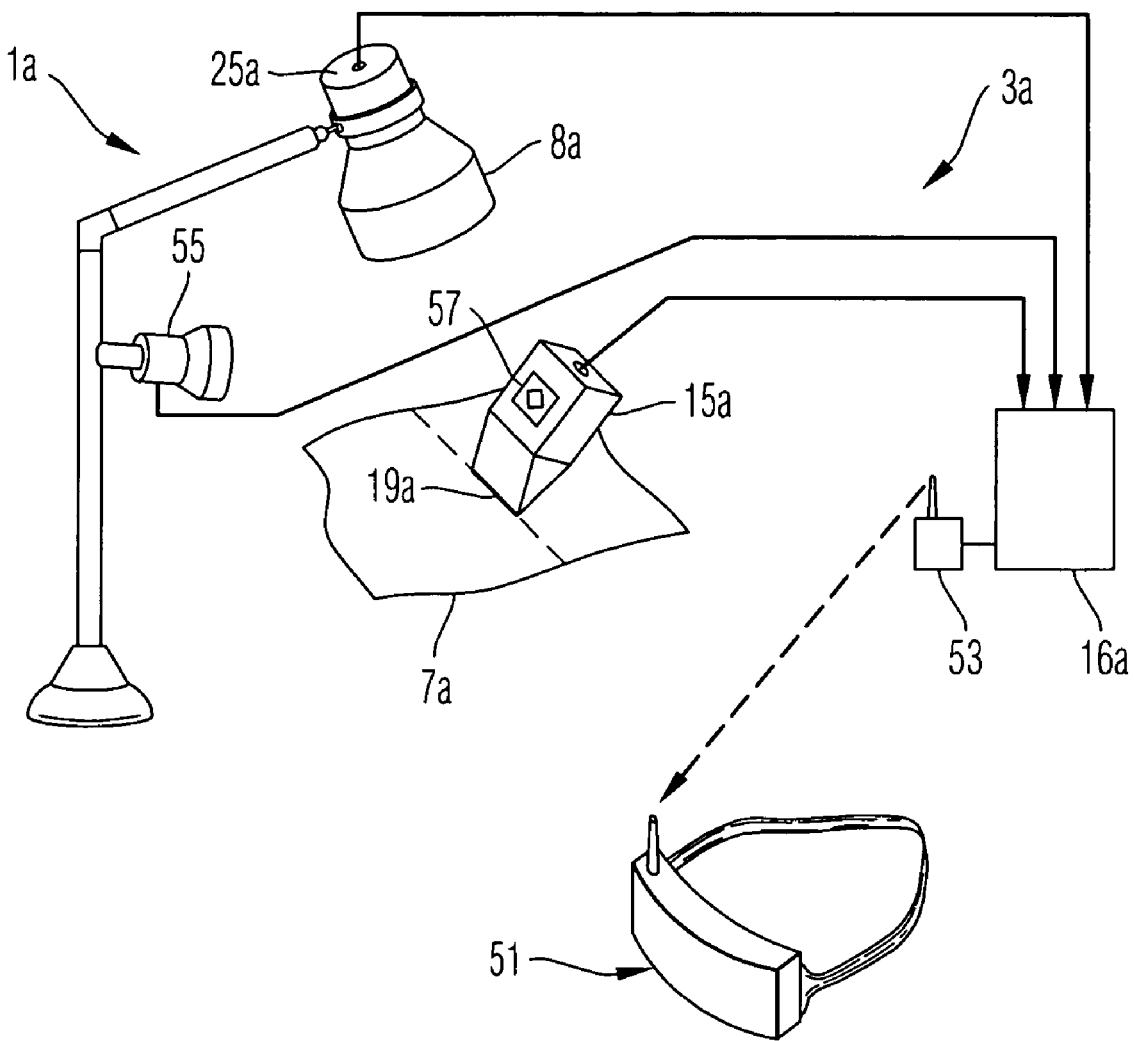
FIG. 4 is a schematic representation of an examination system according to a second embodiment of the present invention.

An examination system 1a shown schematically in FIG. 4 comprises a microscope 3a with an objective lens 8a, a camera 25a and a head-mounted display 51, which can be carried by a viewer directly on his head and which provides both eyes of the viewer with images of a tissue region 7a recorded by the camera 25a through the objective lens 8a. The corresponding image data are supplied by a wireless transmission to the head-mounted display 51 from a computer 16a. The computer 16a receives the data recorded by the camera 25a and is connected to a sender 53 of the wireless transmission.

Different from the embodiment illustrated with reference to FIG. 1, an ultrasonic measuring head 15a of the examination system 1a is a measuring head which samples data not only at its tip, but at plural locations distributed along an extended line 19a. Data sampled by the measuring head 15a at the plural locations along the line 19a are also supplied to the computer 16a for discrimination into different data categories.

A determination of the position of the measuring head 15a relative to the objective lens 8a of the microscope 3a is performed in the examination system 1a not by evaluating the image recorded by the camera 25a, but by evaluating an image recorded by a further camera 55 arranged at a distance from the objective lens 8a. The camera 55 tracks a marker pattern 57 in the form of a square arranged inside of another square provided on a surface of the measuring head 15a, and the computer 16a determines a position and an orientation of the line 19a, along which the measuring head 15a samples data, based on an evaluation of the image recorded by the camera 55. If the evaluation of the data results in a discrimination of the data as "tumor tissue" for one of the plural locations along line 19a, the computer 16a displays a marking at the corresponding image location in the image shown by the head-mounted display 51, as has been illustrated above with reference to FIG. 2.

In the previously described embodiments, it is possible to detect a shift of the examined tissue region within the image field of the microscope by image processing. The markings displayed in the image may then be displaced in accordance with the determined shift, such that re-scanning the examined tissue region with the measuring head may not be necessary after such a shift.

Such shift of the examined tissue region in the image area of the microscope may occur on the one hand due to movements of the patient, and on the other hand due to the surgeon moving the microscope in the operating room relative to the patient. The shift can be detected, e.g. by the computer analyzing the image of the object area 41 (compare FIG. 2), determining the position of tissue structures (compare lines 43 in FIG. 2) as patterns and detecting shifts of such patterns. Thereby, the surgeon is enabled, starting out from a viewing situation as exemplarily shown in FIG. 2 where a region 47 is already provided with markings 45, to shift the microscope so far that the region 47 is no longer within the image area 41, and then to move back the microscope. After moving back the microscope, the markings 45 appear at the correct location in relation to the examined tissue region.

Alternatively to the determination of the shift by image processing as described above, it is also possible in a simplified embodiment only to record the coordinates of the microscope in the operating room and to presume that the patient does not move. The shift to be detected then results from variations of the coordinates of the microscope in the operating room.

The markings are preferably stored in an image memory, the contents of which represent an extended image area which extends beyond the momentarily viewed image area 41 (compare FIG. 2) or the image area displayed by the display 33, respectively. The image area actually displayed then corresponds to a partial region of the image memory, which is reproduced by the display 33. A shift of the image area or the microscope, respectively, then corresponds to shifting or scrolling of the memory contents displayed in relation to the extended image area 41.

The optical system may alternatively or in addition to the microscope also include an endoscope or any video-optical system. Furthermore, if the measuring head is an ultrasonic measuring head, it may also be of a flow detecting Doppler type, or of a duplex type. However, the measuring head may also be adapted to detect biochemical or electrophysical parameters, such as a blood glucose concentration, a sodium or/and potassium concentration or a ratio of same, or a tissue or body fluid temperature.

Summarized, the invention may provide an examination system and a corresponding examination method, comprising: Arranging a tissue region in a vicinity of an object plane of a microscope and generating an optical image of the tissue region, receiving tissue data from a measuring head separate from the microscope, discriminating the tissue data into at least two data categories and displaying markings in the optical image of the tissue region in dependence of the discriminated data category and a relative position between a component of the microscope and the measuring head.

Therefore, while the present invention has been shown and described herein in what is believed to be the most practical and preferred embodiments, it is recognized that departures can be made therefrom within the scope of the invention, which is therefore not be limited to the details disclosed herein but is to be accorded the full scope of the claims so as to embrace any and all equivalent methods and apparatus.

What is claimed is:

1. An examination system for displaying a tissue region to be examined by a viewer, the system comprising:
    an optical system for generating an optical image of the tissue region, the optical system comprising an objective lens;
    a tissue qualifying system having a measuring head for obtaining tissue data, wherein the measuring head is movable relative to the objective lens, the tissue qualifying system further having a computer for analyzing the obtained tissue data and discriminating the obtained tissue data into at least two data categories;
    a position detecting system configured to determine a position of the measuring head relative to the objective lens; and
    an indicating system for optically marking portions of the optical image of the tissue region based on the detected position of the measuring head and on the discriminated data category.

2. The examination system according to claim 1, wherein the measuring head is a handheld measuring head.

3. The examination system according to claim 1, wherein the indicating device comprises a display configured to generate an image representing the marked portions of the optical image, and a first beam splitter for superimposing the generated image with a beam path of the optical system.

4. The examination system according to claim 3, wherein the optical system comprises an objective lens and at least one ocular lens, and wherein a first beam splitter is disposed in the beam path between the objective lens and the ocular lens.

5. The examination system according to claim 4, wherein the optical system further comprises a second beam splitter disposed in the beam path of the optical system, and a camera for recording an image contained in a beam originating from the beam splitter.

6. The examination system according to claim 5, wherein the objective lens, the second beam splitter and the first beam splitter are consecutively disposed in this order in the beam path of the optical system.

7. The examination system according to claim 6, wherein the position detecting system is configured to determine the position of the measuring head based on an image detected by the camera.

8. The examination system according to claim 1, further comprising a camera disposed in a beam path of the optical system, and wherein the position detecting system is configured to determine the position of the measuring head based on an image detected by the camera.

9. The examination system according to claim 8, wherein the image detected by the camera has plural color components, wherein the position detection system is configured to evaluate a first color component of the image, and wherein the indicating system is configured to optically marking the portions of the optical image using a color contained in a second color component of the image different from the first color component of the image.

10. The examination system according to claim 1, wherein the optical system comprises a camera onto which an object plane of the optical system is imaged, and a display device for displaying the image detected by the camera to the viewer.

11. The examination system according to claim 10, wherein the indicating system is configured to optically mark the portions of the optical image using the display device.

12. The examination system according to claim 1, wherein the measuring head comprises at least one of a fluorescence measuring head, a Raman spectroscopy measuring head, an acousto-optical spectroscopy measuring head, an optical coherence tomography measuring head, an ultrasound measuring head, an ultrasonic Doppler measuring head, a concentration measuring head, and a temperature measuring head.

13. The examination system according to claim 1, wherein the measuring head is configured to sample the tissue data at plural locations disposed along a substantially straight line or in an array, and wherein the computer is configured to discriminate the plural data categories corresponding to each of the plural locations.

14. The examination system according to claim 1, further comprising a memory for storing locations of markings, wherein the indicating system is configured to mark the optical image based on stored locations.

15. The examination system according to claim 1, further comprising an image memory for storing image data representing an extended image area larger than an image area of the optical image provided by the optical system.

16. A method of displaying a tissue region, the method comprising:
    arranging the tissue region in a vicinity of an object plane of an optical system and generating an optical image of the tissue region using an objective lens;
    receiving tissue data from a measuring head which is separate from the optical system and which is movable relative to the objective lens;
    discriminating the tissue data into at least two data categories; and
    displaying markings in the optical image of the tissue region based on the discriminated data category and a relative position of the measuring head relative to the objective lens.

* * * * *